United States Patent [19]

Rohrbach et al.

[11] 4,268,423
[45] May 19, 1981

[54] SUPPORT MATRICES FOR IMMOBILIZED ENZYMES

[75] Inventors: Ronald P. Rohrbach, Forest Lake; Mary Maliarik, Lake Forest, both of Ill.

[73] Assignee: UOP Inc., Des Plaines, Ill.

[21] Appl. No.: 95,019

[22] Filed: Nov. 16, 1979

[51] Int. Cl.³ .................... B01J 31/06; C12N 11/14; C12N 11/08
[52] U.S. Cl. .................... 252/430; 435/176; 435/180
[58] Field of Search ............... 252/430; 435/180–182, 435/174–177; 260/6

[56] References Cited

U.S. PATENT DOCUMENTS

| 4,066,504 | 1/1978 | Krasnobajew et al. | 260/6 |
| 4,141,857 | 2/1979 | Levy et al. | 252/430 |
| 4,184,986 | 1/1980 | Krasnobajew et al. | 435/180 |

Primary Examiner—P. E. Konopka
Attorney, Agent, or Firm—James R. Hoatson, Jr.; Raymond H. Nelson; William H. Page, II

[57] ABSTRACT

An improved method of preparing support matrices for immobilization of reactive chemical entities, such as enzymes, comprises deposition of a polyamine on a core support, such as an inorganic oxide, contacting the polyamine-coated core support with a bifunctional reagent which cross-links the polyamine and provides pendant functional groups, and recovering the matrix, wherein the improvement comprises deposition of the polyamine as a thin, uniform film from solvents of low surface tension.

7 Claims, 1 Drawing Figure

Immobilized Enzyme System

Immobilized Enzyme System
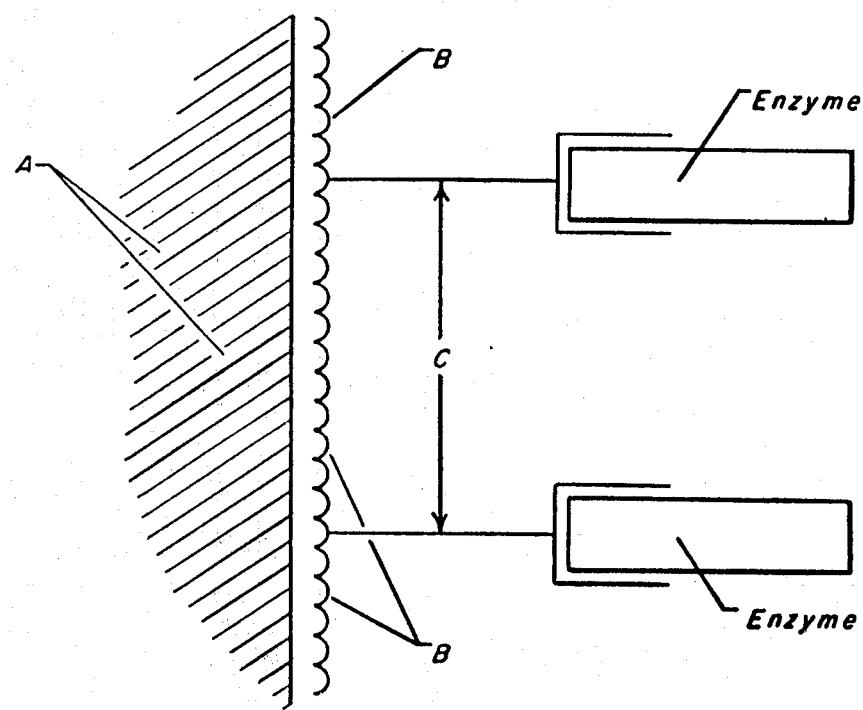

SUPPORT MATRICES FOR IMMOBILIZED ENZYMES

BACKGROUND OF THE INVENTION

Enzyme-catalyzed reactions often have the advantages of proceeding with great chemical specificity under relatively mild conditions, and often accomplish what man finds difficult, if not impossible, to duplicate in the laboratory. For such reasons there is increasing emphasis on the use of enzymatic processes on a commercial scale. One example, of many which could be cited, is the conversion of glucose to fructose using glucose isomerase.

Enzymes are water soluble, and if they are merely used in aqueous solutions recovery of enzyme for reuse is difficult and expensive. Using the enzyme only once affords a process which is relatively expensive. Consequently, many techniques have been developed for immobilizing the enzyme in such a way that substantial enzymatic activity is displayed while the enzyme itself remains rigidly attached to some water-insoluble support, thereby permitting reuse of the enzyme over substantial periods of time and for substantial amounts of feedstock. One illustration of a method for immobilizing an enzyme is found in Levy and Fusee, U.S. Pat. No. 4,141,857, where a polyamine is absorbed on a metal oxide such as alumina, treated with an excess of a bifunctional reagent, such as glutaraldehyde, so as to cross-link the amine, and then contacting the mass with enzyme to form covalent bonds between the pendant aldehyde groups and an amino group on the enzyme. The support matrix prepared according to the aforementioned invention has great utility in immobilizing reactive chemical entities. Enzymes are but one class of such reactive chemical entities.

It is highly desirable that immobilized enzyme systems, i.e., the structure which results from binding of an enzyme to a support matrix, be prepared reproducibly and with maximum enzyme activity, for these are of paramount importance for technological efficiency and commercial success.

SUMMARY OF THE INVENTION

An object of this invention is to provide an improved method of preparing a support matrix used to immobilize reactive chemical entities comprising treating an inorganic solid support with a polyamine, subsequently cross-linking said polyamine with a bifunctional reagent, and recovering the resulting support matrix, wherein the improvement comprises using a liquid of surface tension less than about 30 dynes per centimeter as a solvent for said polyamine so as to more evenly distribute said polyamine on the surface of the solid inorganic support. In one embodiment said inorganic solid support is alumina, said polyamine is polyethyleneimine, said bifunctional reagent is glutaraldehyde, and the polyethyleneimine is deposited from an isopropyl alcohol solution. Other embodiments and objects will be recognized from the description herein.

DESCRIPTION OF THE FIGURE

Many immobilized enzyme systems, such as that described above, have a common conceptual basis which is depicted pictorially in the FIGURE. It is to be understood that enzymes are merely one class of reactive chemical entities which may be immobilized and subsequently utilized in a chemical process.

There is a central core support, A, whose primary purpose is to provide mechanical and thermal stability to the system and which is chemically inert in the enzymatic reaction. The intermediate bonding layer, B, provides an interface between the core and the pendant groups, C. This layer may be held to the core either by physical entrapment, as within the pores of A, by strong short-range physical and/or chemical forces, as by surface adsorption or absorption, by chemical binding to the surface of the core support, or by a combination of the above. The pendant groups, C, may be part of the molecular structure of the binding layer, or may be chemically bonded to a suitable site on the binding layer. Such pendant groups are characterized by the presence of a chemically reactive functionality, usually terminally situated, which can covalently bond to some part of the enzyme, or other reactive chemical entity, sufficiently removed from its "active site" so as not to interfere substantially with its catalytic activity.

DESCRIPTION OF THE INVENTION

This invention relates to an improved method of preparing the structure depicted in the FIGURE and to the resulting improved structure itself. The central core support, A in the FIGURE, may be a metal oxide, preferably alumina and silica, glass, a ceramic or a metal. It needs to provide structural integrity, especially mechanical strength, have good characteristics in a system where there is a liquid flow, and provide a surface, wholly or in part, to which a layer of organic material can be attached either by physical or chemical means, or by a combination of them.

The binding layer, B, may be an organic polymer or a resin. Examples of such binding layers include functionalized polyethylenes, polyamines cross-linked with agents such as dialdehydes and diisocyanates, and others known to those skilled in the art. In a preferred embodiment the binding layer is a polyamine, such as polyethyleneimine, tetraethylenepentamine, ethylenediamine, diethylenetriamine, triethylenetetramine, pentaethylenehexamine, hexamethylenediamine, phenylenediamine, and the like, cross-linked via a reagent selected from the group consisting of dialdehydes and diisocyanates, as for example glutaraldehyde, succindialdehyde, toluenediisocyanate, and the like. In another preferred embodiment the binding layer is a functionalized polystyrene, such as aminopolystyrene, cross-linked by one of the aforementioned agents.

The pendant group, C, may be an independently functionalized group of the polymer, as for example an aldehydic moiety attached via mediating carbon atoms to a polyethylene chain, an independently functionalized group of a resin, or an unreacted terminus of the cross-linking agent wherein the other terminus is covalently bonded to the binding layer. In a preferred embodiment the pendant group arises from a cross-linking agent selected from the group consisting of dialdehydes and diisocyanates.

In some instances the demarcation between core support, A, binding layer, B, and pendant group, C, may seem indistinct. For example, the binding layer may appear to be part of the core, and might even contain a functional group which can covalently bond to an enzyme, thereby providing an immobilized enzyme system. A representative of this class is a chemically modified glass whose surface bears an organic residue having a functional group capable of covalently bonding to an enzyme. This invention relates to such a system, and to all systems which are functionally equivalent to, or can be functionally described by the representation in the FIGURE, however that may be attained in any specific immobilized enzyme system. The combination of the structures, A, B, and C forms a support matrix; addition of enzyme forms an immobilized enzyme system.

The improvement in the method of preparing a support matrix taught herein may be applied to any immobilized reactive chemical entity in which the reactive molecule can react with the pendant functional group without substantial loss of chemical activity. Enzymes form an important class of such reactive molecules, examples of which include glucose isomerase, glucoamylase, lactase, cellulase, glucose oxidase, peroxidase, ribonuclease, urease, histidase, trypsin, papain, hexokinase, chymotrypsin, acylase, invertase, ficin, lysozyme, protease, pepsin, rennin, xylanase, beta amylase, gamma amylase, asparaginase, cholesterol oxidase, alcohol dehydrogenase, amino acid oxidase, collagenase, arginase, catalase, deoxyribonuclease, etc. It is to be understood that these enzymes are cited solely for illustrative purposes and it is not to be construed as a limitation of this invention. Other enzymes may be utilized, but not necessarily with equivalent results.

The Levy and Fusee U.S. Pat. No. 4,141,857, teaches the preparation of a class of support matrices corresponding to the description above. The process of the aforementioned invention is simple and conveniently performed, either in batch or continuous mode, at both a laboratory and commercial scale. For example, an inorganic oxide, such as gamma alumina, may be contacted with an aqueous solution of a polyamine, such as polyethyleneimine, where the polyamine is present at a concentration from about 1% to about 50%. Excess liquid is removed by suitable means, as by decantation, and the oxide is washed with water to remove excess polyamine.

An aqueous solution of cross-linking agent, such as glutaraldehyde, containing from about 1% to 25% of the bifunctional reagent is added in an amount sufficient to provide an excess of from about 3 to about 50 or more moles of said bifunctional reagent per mole of polyamine. This solution is contacted, with occasional mixing, with the polyamine-coated oxide for a time sufficient to ensure equilibrium, generally from about 5 minutes to about 5 hours. Liquid is then removed from the oxide support by suitable means, such as by decantation, and the solid support is washed well with water to remove adhering, but not chemically bound, bifunctional reagent. At this stage the preparation of the support matrix is complete; the support matrix is ready to immobilize reactive chemical entities by covalently bonding them at a suitable site. For example, the matrix may be contacted, with mixing, with a solution of glucose isomerase for about 5 to about 30 hours. Excess liquid may be removed, and the solid may be washed well with water to remove adhering but mobile enzymes. This completes preparation of an immobilized chemical entity, which in this example is an immobilized enzyme system, viz., glucose isomerase.

An unexpected property of immobilized enzyme systems prepared according to the prior art teachings is that the enzyme system so prepared is variable both in appearance and in initial enzymatic activity. That is to say, support matrices prepared at different times, with different batches of oxide, polyamine and bifunctional reagent, when contacted with identical amounts of enzyme, from a common source, afford immobilized enzyme systems of different appearance and substantially different activity. This results even though the distinct support matrices show no analytical differences on chemical examination.

A surprising discovery of this invention is that deposition of the polyamine from solutions in solvents of low surface tension leads to a support matrix which bonds chemically reactive entities, such as enzymes, with uniform and highly predictable results, thereby eliminating problems associated with non-reproducible activity. Another discovery is that the aforementioned method leads to an immobilized enzyme system whose activity is significantly greater than those which have been prepared by prior methods.

The core supports which can be used in the improvement of this invention include all the aforementioned ones. Inorganic oxides are preferred core supports, and gamma alumina is particularly preferred.

Among the polyamines which may be used are ethylenediamine, diethylenetriamine, triethylenetetramine, tetraethylenepentamine, pentaethylenehexamine, hexamethylenediamine, polyethyleneimine, and aminopolystyrene. Solutions of from about 1% to about 50% by weight in polyamine may be employed, but solutions containing less than about 10% of polyamine are preferred. The amount of solution employed may depend on the concentration of polyamine, but in any event a sufficient amount is used so that the total amount of polyamine present is at least 5% by weight of the core support. When impregnation is done in a batch mode, the polyamine solution is contacted with the polyamine solution for a time from about 5 minutes to about 3 hours or longer, preferably from 0.2 to 2.0 hours with intermittent shaking. The temperature is not critical, and one near ambient frequently is convenient.

The improvement of our invention comprises deposition of the polyamine on the core support from a solution of the polyamine in a solvent of low surface tension, by which is meant a liquid as a solvent whose surface tension is less than about 30 dynes per centimeter. One class of such solvents consists of aqueous solutions of surfactants, especially cationic and nonionic surfactants satisfying the stated surface tension requirements. Examples of cationic surfactants include amine oxides (e.g., cetyl dimethylamine oxide) and polyoxyethylene amines (i.e., products derived from the ethoxylation of primary and secondary amines). An example of nonionic surfactants, cited for illustrative purposes only, is the group of polyoxyethylene derivatives which include ethoxylated alkylphenols (e.g., nonylphenoxypoly(ethylenoxy)ethanol), ethoxylated aliphatic alcohols (e.g., stearylpoly(ethylenoxy)ethanol), and polyethylene glycol esters.

Another class of liquids which may be utilized as solvents in this invention consists of organic liquids, especially those miscible with water. Examples include methanol, ethanol, propanol, isopropyl alcohol, acetone, and acetonile. However, liquids immiscible with water also may be used, as exemplified by pentane, hexane, cyclohexane, diethyl ether, and ethyl acetate.

The solvents enumerated above are cited solely for illustrative purposes, and other agents may be used within the scope of this invention but not necessarily with equivalent results.

After the inorganic oxide has been contacted with a solution of the polyamine and impregnation has been completed, excess solution is removed, as by decantation. The coated oxide may be washed with the same solvent to remove loosely adhering polyamine, following which the polyamine-coated inorganic oxide is contacted with a solution of a bifunctional reagent which serves to cross-link the amine and to furnish a pendant functional group which covalently bonds to the reactive chemical entity, as is described above. Examples of said bifunctional reagents include glutaraldehyde, terphthalaldehyde, succindialdehyde, and toluenediisocyanate. Contact time may be from about five minutes to about five hours, with periodic mixing of the phases during this interval. Excess solution is removed, as by decantation, and the solid is washed to remove adhering, but not chemically bound, bifunctional reagent. A procedure which utilizes a solution of the bifunctional reagent in a solvent of low surface tension, and which may be the same as or different from the solvent used for the polyamine, is contemplated as being within the scope of this invention, but may not necessarily afford equivalent results in every case.

This completes the preparation of the improved support matrix. A reactive chemical entity now may be immobilized by suitable means. Using glucose isomerase as an example, immobilization may be performed as previously described.

The examples cited below serve only to illustrate the present invention, and are not to be construed as limitations thereof.

EXAMPLE 1

Gamma-alumina of 60/80 mesh is contacted with occasional mixing with a solution of 5% aminopolystyrene dissolved in isopropyl alcohol, using 5 ml. solution per gm oxide, for about one hour. Excess liquid is removed by decantation, and solid is washed with an equal amount of isopropyl alcohol. The polyamine-coated inorganic oxide is then contacted with an aqueous solution of glutaraldehyde, 2.5% by weight, in an amount of 18 ml per gm alumina. The mixture is shaken intermittently for one hour and the excess liquid is removed by decantation. Solid is thereafter washed with water until the aqueous washings are negative to a fuchsin aldehyde test.

EXAMPLE 2

Gamma-alumina of 60/80 mesh is contacted with occasional mixing with a solution of 5% polyethyleneimine dissolved in water containing a nonionic surfactant, of the ethoxylated aliphatic alcohol type, at a concentration sufficient to provide an initial surface tension less than 30 dynes per centimeter. The amount of solution is 3 ml per gm of inorganic oxide, and the contact time is about 30 minutes. After removal of excess liquid by decantation, the solid may be washed with an equal volume of surfactant solution. Subsequent steps in preparation of the support matrix follow the description of the prior example.

What is claimed is:

1. A method of preparing a support matrix useful for immobilization of an enzymatic material which comprises depositing a polyamine to an inorganic oxide support via a solution containing at least 5% by weight of polyamine per weight of said support wherein said addition of said polyamine is performed in the presence of an aqueous solution of a surfactant selected from the group consisting of cationic and nonionic surfactants having a surface tension of less than 30 dynes per centimeter to produce a polyamine coated-support, removing excess polyamine from said support, and contacting said polyamine-coated support with a solution containing an excess of a bifunctional monomeric material to provide a cross-linkage of said bifunctional monomer with said polyamine of said polyamine-coated support to produce said support matrix.

2. The method of claim 1 wherein the support matrix is comprised of an inorganic oxide support to which is attached a polyamine binding layer, a pendant functional group anchored at the non-functional end to said binding layer, and wherein said functional group is capable of covalently bonding to enzymes.

3. The method of claim 2 wherein said inorganic oxide support is selected from the group consisting of aluminum oxide, silicon oxide, glass and a ceramic material.

4. The method of claim 2 wherein said polyamine binding layer is selected from the group consisting of cross-linked polyamines and cross-linked aminopolystyrenes.

5. The method of claim 4 wherein said polyamine binding layer is selected from the group consisting of polyethyleneimine, tetraethylenepentamine, ethylenediamine, diethylenetriamine, triethylenetetramine, pentaethylenehexamine, hexamethylenediamine, and phenylenediamine, and said bifunctional monomeric cross-linking agent is selected from the group consisting of glutaraldehyde, succindialdehyde, and toluenediisocyanate.

6. The method of claim 1 wherein said surfactant having a surface tension less than about 30 dynes per centimeter is an organic solvent.

7. The method of claim 1 wherein said enzyme is selected from the group consisting of glucose isomerase, glucoamylase, cholesteroloxidase, alcohol dehydrogenase, amino acid oxidase, arginase, asparaginase, catalase, chymotrypsin, cellulase, collagenase, deoxyribonuclease, ficin, histidase, lactase, peroxidase, lysozyme, gamma amylase, papain, rennin, ribonuclease and urease.

* * * * *